US009506860B1

(12) United States Patent
Wimmer

(10) Patent No.: US 9,506,860 B1
(45) Date of Patent: Nov. 29, 2016

(54) APPARATUS FOR THE CALIBRATION OF OPTICAL MEASURING INSTRUMENTS

(71) Applicant: BYK-Gardner GmbH, Geretsried (DE)

(72) Inventor: Severin Wimmer, Munich (DE)

(73) Assignee: BYK-GARDNER GMBH (DE)

( * ) Notice: Subject to any disclaimer, the term of this patent is extended or adjusted under 35 U.S.C. 154(b) by 0 days.

(21) Appl. No.: 15/216,567

(22) Filed: Jul. 21, 2016

Related U.S. Application Data

(63) Continuation of application No. 14/604,182, filed on Jan. 23, 2015, now Pat. No. 9,417,184.

(30) Foreign Application Priority Data

Jan. 23, 2014 (DE) .................... 10 2014 100 774

(51) Int. Cl.
*G01N 21/47* (2006.01)

(52) U.S. Cl.
CPC ....... *G01N 21/4785* (2013.01); *G01N 2201/13* (2013.01)

(58) Field of Classification Search
CPC ........... G06K 7/1417; G01N 27/3274; G01N 2001/2893; G01N 21/4785
See application file for complete search history.

(56) References Cited

U.S. PATENT DOCUMENTS

| 4,291,981 A * | 9/1981 | Ohnishi | G01N 21/4785 356/243.2 |
|---|---|---|---|
| 5,986,769 A | 11/1999 | Krzyminski | 356/445 |
| 6,262,804 B1 | 7/2001 | Friend | 235/462.45 |
| 6,598,800 B1 | 7/2003 | Schmit | 235/462.44 |
| 2005/0139675 A1 | 6/2005 | An | 235/462.24 |
| 2006/0131417 A1 | 6/2006 | Kucher | 235/462.01 |
| 2009/0302123 A1 | 12/2009 | Lugt | 235/494 |
| 2010/0235133 A1 | 9/2010 | Palumbo | 702/116 |
| 2014/0231387 A1 | 8/2014 | Holloway | 216/36 |

OTHER PUBLICATIONS

Japan Trend Shop, http://www.japantrendshop.com/kasmi-paper-weight-ruler-p-1330.html, Feb. 15, 2012.*
Hayato Kawashima "Invisible Two-dimensional Barcode Fabrication inside a Synthetic Fused Silica by Femtosecond Laser Processing Using a Computer-generated Hologram", 2011 SPIE.
Lionson, http://www.lionsons.com/3d_crystal/crystal_block_0011.html, Nov. 19, 2011.
Notice of Allowance issued in U.S. Appl. No. 14/604,182, dated May 10, 2016 (11 pgs).
Office Action issued in U.S. Appl. No. 14/604,182, dated Jun. 30, 2016 (4 pgs).
Office Action issued in U.S. Appl. No. 14/604,182, dated Sep. 24, 2015 (15 pgs).

* cited by examiner

*Primary Examiner* — Kara E Geisel
*Assistant Examiner* — Maurice Smith
(74) *Attorney, Agent, or Firm* — Hayes Soloway P.C.

(57) ABSTRACT

An apparatus for the calibration of optical measuring instruments with a carrier includes a calibration body having a glass body which has at least one scattering element, wherein the scattering element is completely surrounded by the glass body, and wherein a degree of transmission of the scattering element and of the glass body differ from one another.

21 Claims, 2 Drawing Sheets

Fig. 1
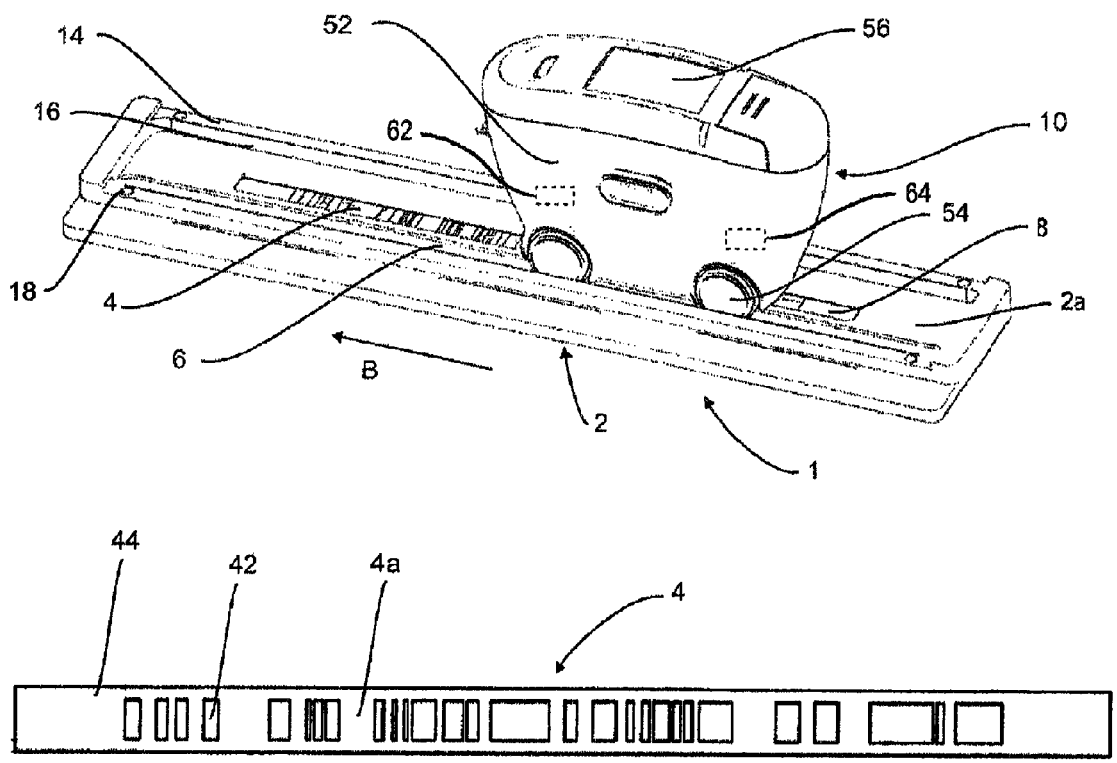
Fig. 2
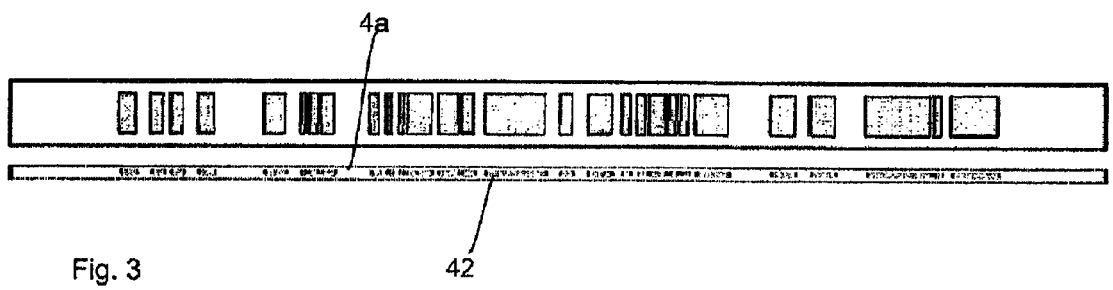
Fig. 3

APPARATUS FOR THE CALIBRATION OF OPTICAL MEASURING INSTRUMENTS

CROSS REFERENCE TO RELATED APPLICATION

This application is a continuation of U.S. patent application Ser. No. 14/604,182, filed Jan. 23, 2015, which application in turn claims priority from German Patent Application Serial No. 102014100774.3, filed Jan. 23, 2014, the contents of which are incorporated herein by reference.

BACKGROUND OF THE INVENTION

The present invention relates to an apparatus for the calibration and/or testing of measuring instruments. Various optical measuring instruments are known from the prior art. The invention relates in particular to a measuring instrument for the investigation of characteristics of surfaces. In addition, instruments of this type have long been known from the prior art. In this case it is known, in particular, for a suitable measuring instrument to be guided over a surface to be investigated and for this surface to be illuminated in this case and for information to be gathered from the radiation reflected or scattered respectively.

In this case it is necessary, however, for these measuring instruments to be newly calibrated from time to time. For this purpose calibration appliances or standards respectively are known from the prior art. These calibration appliances usually have in this case a carrier along which the measuring instrument can be guided, in which case it illuminates a calibration body. Information can be gathered from the radiation thrown back or reflected respectively or scattered accordingly by the calibration body, and calibration or adjustments respectively can be carried out again on the basis of this information. In this case these calibration appliances are frequently subjected to relatively rough handling. In part these calibration appliances are soiled and are cleaned with abrasive cleaning agents. In addition, a change in the respective calibration bodies frequently occurs as a result of ageing processes. In this way, after a certain amount of time they are no longer capable of being used for the purpose intended for them.

The object of the present invention is therefore to improve the resistance and preferably also the durability of calibration appliances of this type.

SUMMARY OF THE INVENTION

An apparatus according to the invention for the calibration of optical measuring instruments has a carrier. In addition, the apparatus has a calibration body arranged on the carrier.

According to the invention this calibration body has a glass body which in turn has at least one scattering element, this scattering element being completely surrounded by the glass body and a degree of transmission of the scattering element and of another region of the glass body differing from each other (in particular with respect to light striking the calibration body). It is advantageous for this calibration body to serve as a calibration standard and/or test standard.

It is therefore proposed according to the invention that a calibration body should be provided which has scattering elements differing optically (with respect to the glass body), but these scattering elements—other than in the prior art—are arranged not on a surface of the calibration body but in an inner space. In this way, the aforesaid scattering elements are not susceptible themselves to damage and soiling and, in addition, to ageing processes and also to cleaning processes.

In the case of a further advantageous embodiment the contacting element or the calibration body respectively is arranged on the carrier in a fixed manner. In this case it is possible for the calibration body to be screwed or glued to the carrier in a fixed manner or to be fastened thereto by other fastening means. In this way, it is possible to ensure that the calibration body cannot shift with respect to the carrier, so that the reliability of the appliance is increased as a whole.

In the case of a further advantageous embodiment the scattering element is a scattering element produced by a laser treatment of the glass body. This means that these scattering elements are produced with the aid of methods known from the prior art in the interior of the glass body, for example by a local melting of the glass material being carried out in the interior. This can be carried out for example by a so-called 3D laser engraving. In this way, it is possible for the scattering element, as mentioned above, to be situated in the interior of the glass body and not on the outer surface thereof.

It is also possible, with the aid of laser treatments or laser irradiation of this type respectively, for the depth—by which the scattering element is produced—inside the glass body to be fixed.

In the case of a further preferred embodiment the carrier has a guide device which guides the measuring instrument to be calibrated in such a way that the measuring instrument is movable with respect to the carrier along a pre-defined line.

It is advantageous for the line along which the measuring instrument can be displaced with respect to the carrier to be a straight line. It would also be possible, however, for the calibration body to be incorporated in a measuring instrument in a stationary manner. In this way, the measuring instrument can have for example an irradiation or illumination device which in normal operation illuminates a material to be investigated and which in a calibration or testing operation illuminates the calibration body. It is preferable in an embodiment of this type for the measuring instrument to have a sensor device which is arranged behind the calibration body in the illumination direction. In the case of an arrangement of this type, the carrier is preferably used to position the calibration body in an unambiguous and, in particular, fixed position.

In this case it is preferable for the calibration body or standard respectively to be held in a ring (i.e. this ring constitutes the carrier in this case) and to be held on a sample well. The ring ensures an exact positioning in order to obtain reproducible measurement values.

In the case of a further advantageous embodiment the guide device has a first guide rail in which at least one wheel of the measuring instrument can roll. Measuring instruments of this type frequently have wheels by means of which they can roll with respect to a surface to be investigated, for example the surface of the bodywork of a motor vehicle. The guide device is designed in such a way that this wheel can also roll with respect to the guide device.

It is advantageous for the apparatus also to have a second guide rail which in a particularly preferred manner is parallel to the first guide rail and in which at least one wheel of the measuring instrument can likewise roll. It is advantageous for the measuring instrument to have four wheels, two of these wheels running in one guide rail in the calibration operation and the other two wheels running in the other guide rail.

It is preferable for the guide rail or the guide device respectively to allow a movement of the measuring instrument in only one direction, but not in a direction at a right angle to this. For this purpose a width of the guide rail can be adapted to a width of the wheels of the measuring instrument, for example it can be selected to be only slightly larger. In addition, protection mechanisms, which prevent damage to outer surfaces of the wheel of the measuring instrument, can be present on or in the guide rail. On account of this special design of the guide rail the measuring instrument is prevented from being capable of being moved transversely to its direction of movement with respect to the carrier.

It is advantageous for the guide rail, or a surface on which the wheel of the measuring instrument rolls respectively, to be situated at substantially the same height as a surface of the calibration body. In this way, an actual measurement situation on a surface, for example of a motor vehicle, can be adjusted in a reliable manner.

It is preferable for the scattering element to scatter light of the apparatus irradiated onto it. It would also be possible, however, for the scattering element to be an element which is reflecting rather than scattering.

In the case of a further advantageous embodiment a transmission or a transmission capability of the scattering element is less than a transmission capability of the areas surrounding the scattering element. It is advantageous for a plurality of scattering elements of this type to be formed in the glass body and these are preferably arranged at a distance from one another along the direction of movement of the measuring instrument. In this way, an undisturbed glass body can be formed for example between the individual scattering elements, and, in this way, it has a very high degree of transmission. It would also be possible, however, for a scattering element with a specified transmission to merge into a further scattering element with a transmission different therefrom.

It would also be possible for a plurality of scattering elements to be arranged one behind the other in such a way that when these scattering elements are read out the measuring instrument emits a specified value. In this way, a specified sequence of the scattering elements in the glass body can also be used for the calibration of the measuring instrument. In other words, it is possible for the scattering elements to be arranged inside the calibration body in the manner of a barcode. This barcode can be characteristic of one or more spatial frequencies (number of the periods per unit of length) of the appliance in this case.

If a measurement value (for example a degree of brightness) is recorded with respect to the spatial frequency, and in particular within the scope of a one-dimensional movement, the level of a measurement value can be influenced with the aid of the production of defined patterns (for example a barcode).

Variations in the brightness are produced for example by the arrangement of specified patterns. In this way for example, the calibration body can have a defined sequence of patterns. If the brightness of a pattern of this type is scanned with the aid of a measuring instrument, the variations in the brightness measured can be converted by mathematical filters into measures for the variation in the brightness of a specified spatial frequency or of a spatial frequency range, which are preferably emitted as measurement values. The patterns or scattering elements respectively can preferably be arranged in such a way that a testing standard is achieved with measurement values in the operating range of the measuring instrument. In this case a brightness scan for example can first be recorded and the values measured (in a spatially dependent manner) in each case can be processed by means of mathematic filters in order to obtain the measurement values dependent upon the spatial frequency in this way.

It is preferable for a plurality of scattering elements with different widths or different lengths of extension respectively (in a direction of movement of the measuring instrument) to be provided.

In the case of a further advantageous embodiment the calibration body is arranged on the carrier in such a way that a surface of the calibration body faces along the pre-set line towards the measuring instrument to be calibrated. This means that the calibration body preferably extends so far that it can be illuminated by an illumination device of the measuring instrument along the entire path thereof with respect to the carrier device.

The invention has also been described in this case to the effect that the measuring instrument is moved with respect to the carrier. It would also be possible, however, for the measuring instrument itself to be at rest as compared with the carrier and, instead, for the calibration body to be moved relative to the carrier and/or the measuring instrument. In this way for example, the calibration body itself could be arranged inside a rail and be moved with respect to this rail. An arrangement of this type would also be advisable for measuring instruments which have no wheels for example.

In addition, a holding device movable with respect to the carrier in a pre-set direction of movement could also be arranged on the carrier. The measuring instrument to be calibrated could be arranged in turn on this holding device. In this way, fastening devices could be present which fix the measuring instrument with respect to the holding device.

In the case of a further advantageous embodiment the surface of the calibration body facing the measuring instrument is a smooth surface. It is preferable for the surface also to be a flat surface. In particular, by means of the provision of a glass body, and in this case again preferably by means of the provision of a smooth glass body, the susceptibility thereof to soiling and cleaners for example can be reduced. In addition, when soiling occurs, it is possible to clean the cleaning body very easily.

In the case of a further advantageous embodiment the calibration body is arranged on the carrier in such a way that only one surface of the calibration body is capable of being contacted. In this way, the calibration body is protected very well from outside influences. In particular, the calibration body is also well protected from soiling in this way. If soiling does nevertheless occur, it can be removed very easily. If, as mentioned above, the calibration body is arranged directly on a part of the carrier, for example glued, the formation of gaps into which dirt can penetrate can also be prevented in this way.

In the case of a further advantageous embodiment the carrier is formed in at least two parts and the calibration body is arranged at least partially between these two parts of the carrier. In this case it is possible for a part of the carrier to have a recess through which the calibration body is visible. It is advantageous in this case for the calibration body to be arranged between the two guide rails mentioned above for the guidance of wheels of the measuring instrument.

The present invention further relates to a calibration body or test body respectively for the calibration and/or testing of optical measuring instruments. In this case this calibration body has a glass body which has at least one scattering element, this scattering element being completely surrounded by the glass body and a degree of transmission of the scattering element and the glass body differing from each other and the calibration body being designed, in addition, in one piece, the scattering element being a scattering element produced by laser treatment of the glass body.

With respect to the calibration body a procedure is therefore also selected according to which the scattering element is incorporated into this calibration body, it being advantageous for this calibration body to be a one-piece glass body. In particular, the treatment by laser allows such an (internal) design of a scattering element.

The design of the scattering element can be influenced by this laser treatment. In particular, the scattering effect and/or the degree of transmission of the scattering elements can be influenced. It is preferable for the calibration body to have scattering elements with different degrees of transmission and/or scattering.

It is advantageous for the calibration body to be produced from a uniform material. It is preferable for the scattering elements to consist of the same material as other areas of the calibration body. It is preferable for the calibration body to consist of borofloat glass.

In the case of a further advantageous embodiment at least one surface of the glass body is a plane and/or a smooth surface. In this way, as mentioned above, the cleaning capacity of this glass body can be improved.

In the case of a further advantageous embodiment a thickness of this glass body is between 1 mm and 30 mm, preferably between 2 mm and 20 mm and in a particularly preferred manner between 3 mm and 7 mm.

These thicknesses of the glass body are suitable in this case in a particular manner for also allowing a high degree of transmission for light on those surfaces in which no scattering elements are present.

In the case of a further advantageous embodiment the glass body has a cuboidal design. Round designs such as for example in the form of (circular) discs, however, would also be possible.

It is advantageous for the scattering element to be at a distance of at least 1 mm from two opposed surfaces. It is advantageous in this case for one of these surfaces to be a surface which faces the measuring instrument in the calibration operation. In this case it is further possible for residual glass bodies to be completely transparent. It would also be possible, however, for the rest of the glass body also not to be transparent or only transparent in part respectively and to have a pre-set scattering proportion. In this case it is also possible for the rest of the glass body also to have been treated by laser action.

In the case of a further advantageous embodiment the glass body has a plurality of scattering elements. It is preferable for these scattering elements to be arranged at a distance from one another at least in part. In addition, it is also possible for these scattering elements to have different lengths with respect to the calibration body along the direction of movement of the measuring instrument.

In the case of a further embodiment a plurality of scattering elements are arranged one behind the other with respect to the calibration body in a direction of movement of the measuring instrument.

In this case it is possible for the scattering element to be designed in the form of flat faces, for example of rectangles. It would also be possible, however, for the scattering elements to be designed in the form of figures, and in particular in the form of signs such as letters. In addition, it is also possible for the calibration body to be produced from a coloured glass.

In the case of a further advantageous embodiment the scattering element or at least one scattering element respectively has a substantially homogeneous structure. This is understood to mean for example that a degree of transmission of this scattering element does not change along a direction of movement of the measuring instrument.

In the case of a further advantageous embodiment at least one surface of the calibration body is provided with a coating, and in particular but not exclusively with a lacquer coating. This can be for example a white coloured surface. It would also be possible for the coating to be made reflecting. In addition, this coating could also be absorbing or kept in a dark colour respectively. In general, it is preferable for at least one surface of the calibration body to be provided with a coating. It is advantageous for this to be a coating which changes a transmission characteristic of the calibration body.

It is preferable for the coating to be a homogeneous coating. It would also be possible, however, for the coating to be deliberately non-homogeneous, for example a degree of reflection of this coating changes in the direction of movement of the measuring instrument with respect to the calibration body.

It is advantageous for the aforesaid coating to be provided on that surface which is opposite the surface of the calibration body which faces the measuring instrument. In this way, it is advantageous for this coating or layer of lacquer respectively to be provided on a surface of the calibration body which faces away from the measuring instrument. It is advantageous for the calibration body also to have a constant thickness along the direction of movement of the measuring instrument with respect to the calibration body.

In addition, the coating could also be provided as a scattering coating.

The present invention further relates to the use of a laser-treated glass body for the calibration and/or testing of optical measuring instruments, and in particular for the calibration of those optical measuring instruments which are used for the detection of properties of surfaces. It is advantageous for this to be a glass body of the type described above, in the internal structure of which scattering elements have been formed by means of a laser treatment. It is advantageous in this case for the laser-treated glass body to be used in such a way that the measuring instrument to be calibrated is moved and/or adjusted or arranged respectively relative to the measuring body for the calibration and illuminates the latter at least for a time. In addition, the measurement values output by the measuring instrument can be monitored and, in particular, compared with reference values.

BRIEF DESCRIPTION OF THE DRAWINGS

Further advantages and embodiments are evident from the accompanying drawings. In the drawings FIG. 1 is an illustration of an apparatus according to the invention for the calibration of measuring instruments;

FIG. 2 is a plan view of a calibration body;

FIG. 3 is a further plan view and a side view of a calibration body according to the invention;

DETAILED DESCRIPTION OF THE INVENTION

Figure 4:
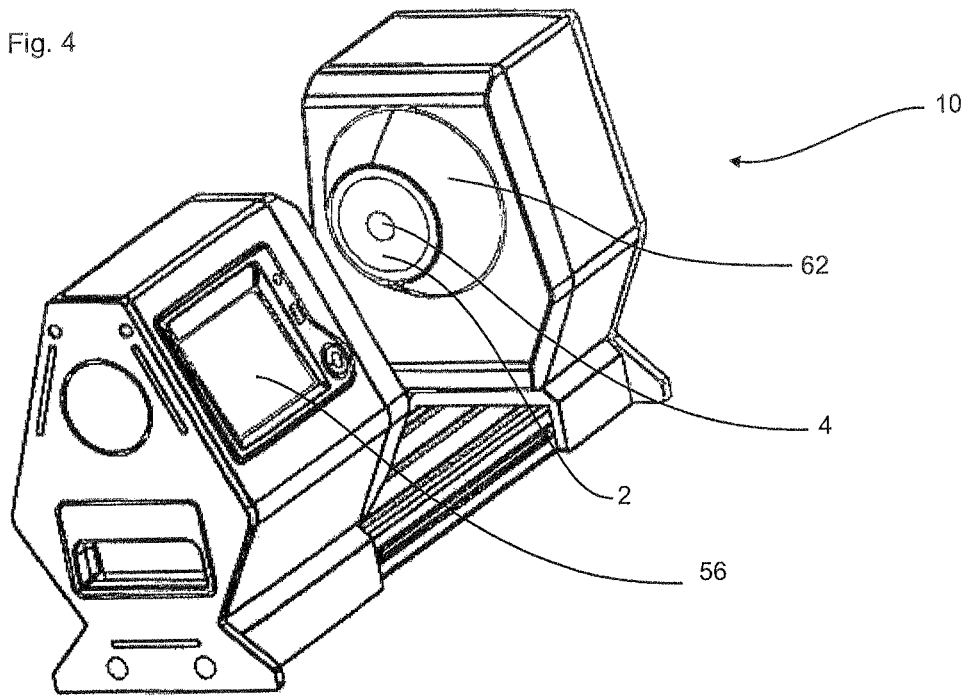
FIG. 4 shows a further embodiment of the present invention.

FIG. 1 shows an apparatus 1 according to the invention for the calibration of optical measuring instruments, a measuring instrument 10 being involved in this case which is used for investigating properties of surfaces, in particular of motor vehicle surfaces.

This measuring instrument has in this case a housing 52 in the interior of which at least one radiation device 62 and at least one radiation detector device 64, both shown in phantom, are preferably arranged. In addition, the measuring instrument 10 has a display 56 with the aid of which information can be output to the user. On its underside or the side facing the carrier 2 respectively the measuring instrument 10 has an opening (not visible) through which radiation, and in particular light, can emerge from the measuring instrument 10. Expressed in more precise terms, this light can strike the calibration body.

The reference number 54 refers to wheels which are arranged on the housing or on the measuring instrument respectively and by which the measuring instrument can be moved with respect to a surface to be investigated.

The reference number 2 refers to a carrier of the calibration apparatus. This carrier 2 serves in this case for guiding the measuring instrument 10. For this purpose the carrier 2 has two guide rails or guide devices or guide rails 6 respectively. These guide rails can have in this case running faces for the measuring instrument. These guide rails extend in this case in the direction of movement B of the measuring instrument and have the effect that, although the measuring instrument can be moved in this direction, it cannot be moved in a direction at a right angle to this. It would also be possible for the carrier to have arranged on it only lateral guides which prevent a lateral transverse movement of the measuring instrument with respect to the carrier 2.

The reference number 4 designates a calibration body which is arranged on the carrier. In particular, this calibration body 4 is glued to an upper part 2a of the carrier 2.

The reference number 8 designates a recess or a hole respectively through which the calibration body 4 or the surface thereof respectively is accessible and, in this way, can also be irradiated by an illumination device of the measuring instrument 10. The reference number 14 designates a lateral edge which bounds the carrier but which also prevents a movement of the measuring instrument 10 in a direction at a right angle to the direction of movement B.

The reference number 16 designates a protection mechanism which is attached to this lateral edge and which for example prevents surfaces of the individual wheels 54 from being scraped. This protection mechanism can be for example a protective film which is attached, for example glued, to the carrier. The reference number 18 designates a fastening element by which the two parts of the carrier 2 are fixed to each other.

FIG. 2 is a plan view of a calibration body 4. This calibration body has in this case a plurality of scattering elements 42 as well as a transparent main body 44 which in this case adjoins the scattering elements in each case. In the case of the embodiment shown in FIG. 2 the transparency of the portion 44 of the main body is very high and the transparency of the scattering elements is lower as compared with the latter. In this case the scattering elements are preferably arranged in such a way that different spatial frequencies of the measuring instrument can be taken into consideration.

FIG. 3 shows a comparison of a plan view with a side view of a calibration body 4. The surface 4a of the calibration body, which faces the measuring instrument during operation, is again evident in this case. It will be noted that the individual scattering elements 42 are embedded in the calibration body or the glass body thereof respectively and, in this way, are not accessible from any side (for a user). In this way, it is possible to ensure that these scattering elements are not susceptible to mechanical influences on the one hand, but are also not subject to any ageing process on the other hand.

FIG. 4 shows a further embodiment or application respectively of the present invention. In the case of this embodiment the measuring instrument 10 to be tested is an instrument in which an illumination device illuminates the inner wall of a (spherical) body by way of a sample to be investigated (or through the latter respectively). For the purpose of testing and/or calibration, instead of the sample to be investigated, the calibration body is pressed into the beam path between the illumination device and at least one sensor device. In the case of this embodiment no relative movement therefore takes place between the measuring instrument and the calibration body 4. The reference number 62 designates a spherical body into which the light is irradiated through the sample (or the calibration body respectively).

The reference number 2 refers in turn to the carrier, on which the calibration body 4 is arranged.

Figure 5:
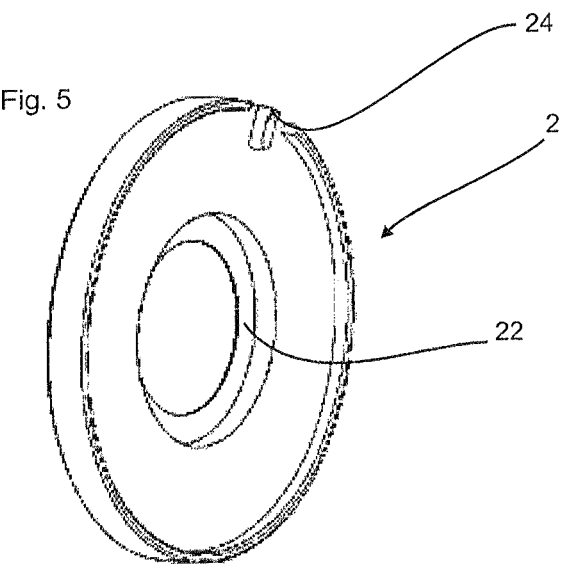
FIG. 5 is an enlarged illustration of the carrier.

FIG. 5 is an enlarged illustration of the carrier 2. The latter has an annular holding body for holding the calibration body. The reference number 24 designates a projection by which it is possible to ensure that the carrier is fastened on the measuring instrument in a precisely defined rotational setting. The reference number 22 designates a carrying body such as for example a carrying ring for carrying or holding respectively the calibration body 4.

All the features disclosed in the application documents are claimed as being essential to the invention, insofar as they are novel either individually or in combination as compared with the prior art.

LIST OF REFERENCES 1 apparatus according to the invention
2 carrier
2a upper part
4 calibration body
4a surface
6 guide devices
8 recess
10 measuring instrument
14 lateral edge
16 protection mechanism
18 fastening element
22 carrying body
24 projection
42 scattering elements
44 portion of the main body
52 housing
54 wheels
56 display
62 spherical body
B direction of movement

The invention claimed is:
1. An apparatus for the calibration and/or testing of optical measuring instruments, said apparatus comprising:
a carrier and a calibration body arranged on the carrier, wherein the carrier comprises a guide which surrounds the calibration body and guides the measuring instrument with respect to the carrier,
wherein the calibration body has a glass body wherein a plurality of scattering elements is formed in an internal structure of said glass body by the arrangement of specified patterns, wherein the scattering elements are completely surrounded by the glass body and is situated in an interior of the glass body, wherein a degree of transmission or degree of scattering respectively of the scattering element and of the glass body differ from one another.

2. The apparatus according to claim 1, wherein the scattering element is produced by a laser treatment of the glass body.

3. The apparatus according to claim 1, wherein the guide guides the measuring instrument with respect to the carrier along a pre-defined line.

4. The apparatus according to claim 3, wherein the calibration body comprises a smooth surface.

5. The apparatus according to claim 3, wherein the guide allows a movement of the measuring instrument in only one direction, but not in a direction at a right angle thereto.

6. The apparatus according to claim 1, wherein the calibration body is arranged on the carrier such that a surface of the calibration body faces along a pre-set line towards the measuring instrument to be calibrated.

7. The apparatus according to claim 1, wherein the calibration body is arranged on the carrier such that in a manner dependent upon a position of the measuring instrument with respect to the carrier an illuminator of the measuring instrument illuminates the at least one scattering element or a further region of the glass body, the transmission of which differs from that of the scattering element.

8. The apparatus according to claim 1, wherein the calibration body is arranged on the carrier such that only one surface of the calibration body is exposed to mechanical contact.

9. The apparatus according to claim 1, wherein the glass body has a plurality of scattering elements with different widths or different lengths of extension respectively.

10. The apparatus according to claim 1, wherein the scattering element is at a distance of at least 1 mm from two opposed surfaces, wherein one of these surfaces faces the measuring instrument in the calibration operation.

11. The apparatus according to claim 1, wherein a transmission capability of the scattering element is less than a transmission capability of the areas surrounding the scattering element.

12. The apparatus according to claim 1, wherein the plurality of scattering elements are arranged at a distance form one another along the direction of movement of the measuring instrument.

13. An apparatus for the calibration and/or testing of optical measuring instruments, said apparatus comprising:
a calibration body for the calibration and/or testing of optical measuring instruments,
a carrier and a calibration body arranged on the carrier, wherein the carrier comprises a guide which surrounds the calibration body and guides the measuring instrument with respect to the carrier, said calibration body having a glass body wherein a plurality of scattering elements is formed in an internal structure of said glass body in the form of flat faces, wherein the scattering elements are completely surrounded by the glass body and is situated in an interior of the glass body, wherein a degree of transmission of the scattering element and the glass body differ from each other, wherein the calibration body is designed in one piece.

14. The calibration body according to claim 13, wherein at least one surface of the glass body is a plane and/or a smooth surface.

15. The calibration body according to claim 13, wherein the scattering element has a substantially homogeneous structure.

16. The calibration body according to claim 13, wherein at least one surface of the calibration body has a coating.

17. The calibration body according to claim 13, wherein the glass body has a plurality of scattering elements with different widths or different lengths of extension respectively.

18. A process for calibrating and/or testing of optical measuring instruments comprising employing a laser treatment on the calibration body of claim 1.

19. The process according to claim 18, wherein scattering elements are formed in an internal structure of the glass body by a laser treatment.

20. The calibration body according to claim 13, wherein the scattering elements are designed in the form of figures or signs such as letters.

21. The calibration body according to claim 13, wherein the scattering elements are arranged at a distance from one another at least in part.

* * * * *